United States Patent
Fitzgibbon

(10) Patent No.: US 7,008,362 B2
(45) Date of Patent: Mar. 7, 2006

(54) TOOL HOLDER ARRANGEMENT

(75) Inventor: Russell Patrick Fitzgibbon, High Wycombe (GB)

(73) Assignee: Armstrong Healthcare Limited, High Wycombe (GB)

( * ) Notice: Subject to any disclaimer, the term of this patent is extended or adjusted under 35 U.S.C. 154(b) by 29 days.

(21) Appl. No.: 10/705,681

(22) Filed: Nov. 12, 2003

(65) Prior Publication Data

US 2004/0142803 A1  Jul. 22, 2004

(30) Foreign Application Priority Data

Jan. 20, 2003 (GB) ................................. 0301242

(51) Int. Cl.
*B23Q 3/155* (2006.01)
*A61B 17/00* (2006.01)

(52) U.S. Cl. .................... 483/9; 483/901; 483/12; 901/41; 901/49; 606/1

(58) Field of Classification Search ............. 483/9, 483/8, 7, 10–12, 16, 901; 901/41, 49; 606/34, 606/4, 10–12, 37, 1; 607/1
See application file for complete search history.

(56) References Cited

U.S. PATENT DOCUMENTS

| 4,620,362 | A | | 11/1986 | Reynolds |
| 4,784,421 | A | * | 11/1988 | Alvité ........................ 483/901 |
| 5,018,266 | A | | 5/1991 | Hutchinson et al. |
| 5,413,573 | A | * | 5/1995 | Koivukangas ................. 606/1 |
| 5,749,885 | A | * | 5/1998 | Sjostrom et al. ............ 606/170 |
| 6,068,627 | A | * | 5/2000 | Orszulak et al. .............. 606/34 |
| 6,840,895 | B1 | * | 1/2005 | Perry et al. ................ 483/901 |
| 2002/0072736 | A1 | | 6/2002 | Tierney et al. |

FOREIGN PATENT DOCUMENTS

JP 10-34471 A * 2/1998

* cited by examiner

Primary Examiner—Erica Cadugan
(74) Attorney, Agent, or Firm—Egbert Law Offices

(57) ABSTRACT

A tool identification system has a tool holder allowing removable attachment thereto of any one of a plurality of tools; a sensor arrangement operable to sense features present on a tool attached to the tool holder; a processor operable to identify uniquely, from the sensed features, the type of the tool attached to the tool holder; and an insulation arrangement provided between the tool holder and the sensor arrangement, thereby electrically insulating the tool holder from the sensor arrangement.

18 Claims, 1 Drawing Sheet

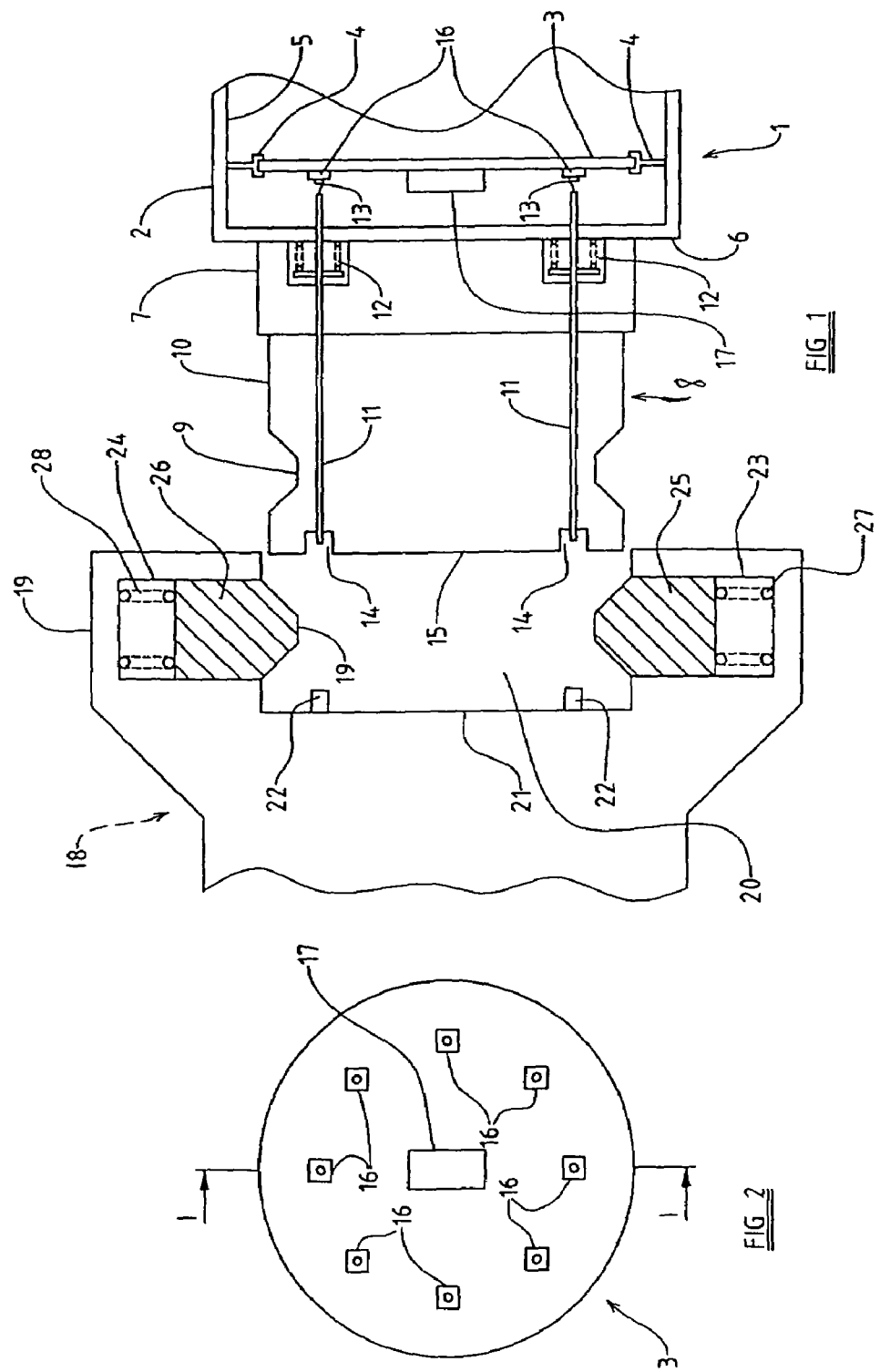

TOOL HOLDER ARRANGEMENT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention relates to a tool holder arrangement, and in particular concerns a tool holder arrangement incorporating a system for uniquely identifying a surgical tool attached to a tool holder.

BACKGROUND OF THE INVENTION

The use of medical robots has become widespread in recent years, in particular for surgical procedures requiring a high degree of precision, for instance minimal access or "keyhole" surgery.

Typically, a medical robot comprises an arm which is movable under computer control, and to which any one of several different tools may be attached. During the course of a surgical procedure, several different tools may be required, and each will be attached in turn to the arm of the medical robot.

Because the tools must be sterile to qualify for use in surgical procedures, conventional identification means such as labeling or marking may not be available for the purpose of distinguishing between tools. In addition, electrical safety and clinical practice requires that the patient is electrically "floating", that is, isolated from any power sources and not earthed. Hence, when the tool contacts the patient during a surgical procedure, this contact must not provide a ground path through which current could flow between the patient and ground.

Because a medical robot is a safety-critical device, it is a requirement in most jurisdictions for medical robots to be immune from single-point failures. In other words, it is preferable for there to be two independent means for verifying which tool is attached to the arm of the robot.

Object of the Invention

The present invention seeks to alleviate some or all of the difficulties.

BRIEF SUMMARY OF THE INVENTION

According to this invention there is provided a tool holder arrangement including: a tool holder to be mounted on a support and allowing removable attachment thereto of any one of a plurality of tools; a sensor arrangement operable to sense at least one feature present on a tool when attached to the tool holder, being a feature or features unique to the specific tool; and a processor operable to identify uniquely, from the sensed feature or features, the type of the tool attached to the tool holder, the tool holder and the sensor arrangement being such that a tool is electrically isolated from the support when the tool is attached to the tool holder.

Preferably the sensor arrangement is operable to sense at least one feature present on a tool in the form of a projection on the tool.

Alternatively the sensor arrangement is operable to sense at least feature present on a tool in the form of a recess on the tool.

Conveniently the sensor arrangement includes a plurality of axially movable rods extending to a face of the tool holder which is adjacent the tool when the tool is attached to the tool holder, there being a respective switch element actuable in response to movement of each of the rods.

Preferably each rod is resiliently biased to an initial position by me a spring.

Advantageously the rods are evenly angularly spaced about the circumference of a notional circle.

Alternatively the rods are arranged in linear co-alignment.

In a further modified embodiment of the invention the sensor arrangement is operable to sense at least one feature present on the tool in the form of a magnetic element.

Preferably the sensor arrangement includes a plurality of detectors responsive to a magnetic field.

Advantageously the tool holder incorporates a connector element to which the tool may be mounted, the connector element being formed of or mounted on an element of insulating material.

Preferably the processor is adapted to generate an alarm signal if only one said feature on a tool is detected.

The tool holder may be provided in combination with at least one tool.

Conveniently the tool is provided with two projecting elements positioned to be co-aligned with two said rods.

In an alternative embodiment the tool is provided with two recesses positioned to be co-aligned with two said rods.

In a further alternative embodiment the tool is provided with two magnetic elements positioned to be co-aligned with two said detectors.

The tool holder arrangement may be incorporated into a robot.

BRIEF DESCRIPTION OF THE SEVERAL VIEWS OF THE DRAWINGS

In order that the present invention may be more readily understood, embodiments thereof will now be described, by way of example, with reference to the accompanying drawings FIG. 1 is a schematic cut-away view of part of an arm provided a tool holder arrangement in accordance with the invention, and a tool.

FIG. 2 is a schematic elevational view of a printed circuit suitable for use with the present invention.

DETAILED DESCRIPTION OF THE INVENTION

Referring to FIG. 1, a tool-receiving end 1 of the arm of a medical robot is shown. The tool-receiving end comprises a housing 2, which is substantially circular in cross section. A substantially circular printed circuit board (PCB) 3 is provided within the housing, the PCB 3 being of slightly smaller radius than the housing 2, and being arranged to be coaxial therewith. The PCB 3 is held in place by suitable mounts 4, which are each attached to an interior surface 5 of the housing 2.

Supported on a front surface 6 of the housing 2 is a substantially cylindrical insulating block 7, which is formed from a substantially electrically non-conducting material.

The insulating block 7 is also arranged to be substantially coaxial with the tool-receiving end 1. Mounted on the insulating block 7, on the opposite side thereof from the tool-receiving end 1, is a connector 8, which is substantially cylindrical (and again coaxial with the tool-receiving end 1), but which has a groove 9 running around the outer circumferential surface 10 thereof. The groove 9 has a flat bottom and the side walls thereof are inclined to the bottom. In an alternative arrangement the connector 8 is of insulating material.

Eight rods 11 are provided, which pass through bores which extend through the connector 8, the insulating block 7 and into the interior of the housing 2. The rods 11 are mounted within respective bores in the connector 8, the insulating block 7 and the housing 2. The bores are parallel and evenly angularly spaced about the circumference of a notional circle. The rods 11 are formed from electrically non-conducting material.

Helical springs 12 are provided around portions of each of the rods 11, in enlarged chambers formed at the end of each bore. One end of each spring 12 engages the outer surface 6 of the housing 2, and the other end of each spring 12 engages a flange on the respective rod 11 so that, in a resting position of the spring 12, the rod 11 is held so that a proximal end 13 thereof rests close to the PCB 3. It will be understood that, if any of the rods 11 are pushed inwardly towards the PCB 3, the respective spring 12 will act to oppose this motion, and once the pushing force is removed the spring 12 will return the rod 11 to its resting position.

Indentations 14 are provided in the end of the connector 8, the indentations being substantially cylindrical and each being centered around a respective one of the rods 11. The connector 8 is configured so that each rod 11 protrudes into the space formed by an indentation 14 when in the resting position but does not protrude past a front surface 15 of the connector 8.

The PCB 3 is provided with eight micro-switches 16 (as can be seen from FIG. 2), which are equi-angularly spaced about the circumference of a notional circle. The arrangement of these micro-switches 16 is such that a respective micro-switch 16 lies opposite the proximal end 13 of each rod 11 when the rods 11 are in their resting positions. A processor 17 is mounted on the PCB 3, the processor being connected to the micro-switches 16.

A connecting portion 18 of a surgical tool is also shown in FIG. 1. The connecting portion 18 is formed at the end of a shank of the tool. The connecting portion 18 comprises a collar 19 which surrounds a circular recess 20. The recess 20 has a base 21. Provided on the base 21 are two spaced-apart protrusions in the form of axially extending pins 22.

The collar 19 is provided, at diametrically opposed positions, with two radially inwardly directed cylindrical recesses 23, 24. Each recess 23, 24 contains a sliding detent element 25, 26, there being a respective spring 27, 28 between the base of each detent 25, 26 and the base of the respective recess 23, 24. The springs 27, 28 serve to bias the detents 25, 26 radially inwardly. The inwardly protruding end of each detent 25, 26 which extends into the recess 20 has a configuration corresponding to that of the groove 9. The detents 25, 26 may thus form a "snap" coupling with the recess 9, securing the tool which is provided with the connecting portion 18 to the connector 8. A projection (not shown) provided on the connecting portion 18 may engage a key-way (not shown) provided on the connector 8 so that the tool may only be mounted on the connector in a specific predetermined orientation.

Upon releasing the tool from the arm of the medical robot, the spring will remove the rods 11 from engagement with the micro-switches 16.

It will be appreciated that, with the above-described system, four different tools can be provided, each with a connecting portion 18 as described, but with the two pins 22 on each of the connecting portions 18 being provided in different locations so as to correspond to a different pair of micro-switches 16. Ideally, each tool will have pins 21 at locations to correspond to two micro-switches 16, neither of which is also associated with any other tool. Hence, either of the two micro-switches 16 that are activated when a particular tool is attached to the arm of the medical robot can be used by the processor 17 to identify uniquely the type of the tool. However, if both switches are closed, effectively there is a double confirmation of the identity of the tool.

Of course, a greater number of micro-switches 16 may be provided PCB 3, to accommodate a greater variety of possible tool types.

In preferred embodiments of the prevent invention, an alarm is raised if only one micro-switch 16 is activated, or if a combination of two or more micro-switches 16 that do not correspond to an individual tool are activated.

In the above-described example, the circular arrangement of the micro-switches 16 means that the tool must be attached to the arm of the medical robot in a certain predetermined orientation. However, in alternative embodiments, the micro-switches 16 are arranged so that, irrespective of the orientation with which the tool is attached to the arm of the medical robot, the tool can be correctly identified. For instance, the micro-switches 16 may be arranged in a substantially straight line extending from the center of the PCB 3 to an edge thereof, with each tool being provided with two concentric rings of pins, similar to the pins 22, on the base 21 of the recess 20. The distance of each of the rings or pins from the center of the base 21 indicates which type of tool it is, and clearly micro-switches 16 at certain distances from the center of the PCB 3 will be activated when this system is employed, irrespective of the relative orientations of the tool and arm.

In an alternative embodiment of the present invention, each tool may be provided with indentations, rather than pins 22, in the base 21 of the recess 20 thereof. In this embodiment, the ends of the rods 11 may protrude past the forward-facing surface 15 of the connector 8, and it will be understood that the tool can then be identified from a combination of two micro-switches 16 that are not activated when the tool is connected to the arm of the medical robot.

It is also envisaged that the present invention may operate by the presence of one or more magnets on the tool, with the connecting portion 18 of the arm of the medical robot being provided with a number of magnetic detectors. When the tool and the arm are connected to one another the magnetic detectors such as Hall effect switches or magnetic reed switches will lie directly opposite the magnets and will be able to detect the presence thereof.

It will be understood that a preferred embodiment of the present invention provides a reliable system of uniquely identifying tools attached to the arm of a medical robot, while maintaining electrical insulation between the tool and the arm, and which alleviates many difficulties associated with the prior art.

In the present Specification "comprises" means "includes or consists of" and "comprising" means "including or consisting of".

The features disclosed in the foregoing description, or the following Claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

I claim:

1. A tool holder arrangement comprising:
   a tool holder to be mounted on a support and allowing removable attachment thereto of any one of a plurality of tools;
   a sensor arrangement operable to sense at least one feature present on one of said tools when attached to the tool holder, wherein said feature or features are unique to the specific one of said tools; and
   a processor operable to identify uniquely, from the sensed feature or features, a type of the tool attached to the tool holder,
   wherein the tool holder and the sensor arrangement are such that a tool of the plurality of tools is electrically isolated from the support when the tool is attached to the tool; and
   wherein the sensor arrangement includes a plurality of rods, each having a longitudinal axis and being axially movable relative the support and the tool holder, extending to a face of the tool holder which is adjacent the tool when the tool is attached to the tool holder, there being a respective switch element actuable in response to movement of each of the rods.

2. A tool holder arrangement according to claim 1, wherein the sensor arrangement is operable to sense at least one feature present on a tool of the plurality of tools in the form of a projection on the tool.

3. A tool holder arrangement according to claim 1, wherein each rod is resiliently biased to an initial position by means of a spring.

4. A tool holder arrangement according to claim 1, wherein the rods are evenly angularly spaced about the circumference of a circle.

5. A tool holder arrangement according to claim 1, wherein the tool holder incorporates a connector element to which the tool may be mounted, the connector element being comprised of or mounted on an element of insulating material.

6. A tool holder arrangement according to claim 1 wherein the sensor arrangement is operable to sense two of said features on a tool.

7. A tool holder arrangement according to claim 6, wherein the processor is adapted to generate an alarm signal if only one said feature on a tool is detected.

8. A tool holder according claim 1, further comprising at least one tool of said plurality of tools.

9. A tool holder according to claim 8, wherein the tool is provided with two projecting elements positioned to be co-aligned with two of said rods.

10. A robot comprising a tool holder arrangement according claim 1.

11. A tool holder arrangement comprising:
    a tool holder to be mounted on a support and allowing removable attachment thereto of any one of a plurality of tools;
    a sensor arrangement operable to sense two features present on one of said tools when attached to the tool holder, the features being unique to a specific one of said tools and
    a processor operable to identify uniquely, from the sensed features, the type of tool attached to the tool holder,
    wherein the tool holder and the sensor arrangement are such that the tool is electrically isolated from the support when the tool is attached to the tool holder;
    wherein the sensor arrangement includes a plurality of rods, each having a longitudinal axis and being axially movable relative the support and the tool holder, extending to a face of the tool holder which is adjacent the tool when the tool is attached to the tool holder, there being a respective switch element actuable in response to movement of each of the rods.

12. A tool holder arrangement according to claim 11, wherein the sensor arrangement is operable to sense at least one feature present on a tool of the plurality of tools in the form of a projection on the tool.

13. A tool holder arrangement according to claim 11, wherein each rod is resiliently biased to an initial position by means of a spring.

14. A tool holder arrangement according to claim 11, wherein the rods are evenly angularly spaced about the circumference of a notional circle.

15. A tool holder arrangement according to claim 11, wherein the tool holder incorporates a connector element to which the tool may be mounted, the connector element being comprised of or mounted on an element of insulating material.

16. A tool holder arrangement according to claim 11, wherein the processor is adapted to generate an alarm signal if a combination of two or more switch elements are actuated which do not correspond to an individual tool.

17. A tool holder according claim 11, further comprising at least one tool of said plurality of tools.

18. A tool holder according to claim 11, wherein the tool is provided with two projecting elements positioned to be co-aligned with two of said rods.

* * * * *